US005567510A

United States Patent [19]
Patnode et al.

[11] Patent Number: 5,567,510
[45] Date of Patent: Oct. 22, 1996

[54] DISPERSIBLE COMPOSITIONS AND ARTICLES AND METHOD OF DISPOSAL FOR SUCH COMPOSITIONS AND ARTICLES

[75] Inventors: Gregg A. Patnode, Woodbury; John E. Bruno, Franconia Township, Chisago County; Denise R. Rutherford, Oakdale; Walter B. Sandison, St. Louis Park, all of Minn.; Dietmar Schlei, Hudson Township, St. Croix County, Wis.

[73] Assignee: Minnesota Mining and Manufacturing Company, St. Paul, Minn.

[21] Appl. No.: 452,795

[22] Filed: May 30, 1995

Related U.S. Application Data

[62] Division of Ser. No. 367,026, Dec. 30, 1994, Pat. No. 5,472,518.

[51] Int. Cl.$^6$ .................................................. D04H 1/58
[52] U.S. Cl. ........................... 428/288; 428/296; 428/903
[58] Field of Search ................................. 428/296, 903, 428/288

[56] References Cited

U.S. PATENT DOCUMENTS

| | | | |
|---|---|---|---|
| H1340 | 7/1994 | Yetter et al. | 604/376 |
| 3,480,016 | 11/1969 | Costanza et al. | 128/284 |
| 3,546,716 | 12/1970 | Laumann | 4/112 |
| 3,804,092 | 4/1974 | Tunc | 128/284 |
| 3,809,088 | 5/1974 | Ulrich, Jr. | 128/285 |
| 4,343,931 | 8/1982 | Barrows | 528/291 |
| 4,372,311 | 2/1983 | Potts | 128/287 |
| 4,529,792 | 7/1985 | Barrows | 528/291 |
| 4,534,349 | 8/1985 | Barrows | 128/334 R |
| 4,620,999 | 11/1986 | Holmes | 428/35 |
| 4,826,493 | 5/1989 | Martini et al. | 604/327 |
| 4,880,592 | 11/1989 | Martini et al. | 264/514 |
| 4,908,278 | 3/1990 | Bland et al. | 428/500 |
| 5,025,052 | 6/1991 | Crater et al. | 524/104 |
| 5,076,983 | 12/1991 | Loomis et al. | 264/101 |
| 5,099,026 | 3/1992 | Crater et al. | 548/229 |
| 5,125,995 | 6/1992 | D'Haese et al. | 156/155 |
| 5,181,966 | 1/1993 | Honeycutt et al. | 134/42 |
| 5,181,967 | 1/1993 | Honeycutt | 134/42 |
| 5,200,247 | 4/1993 | Wu et al. | 428/131 |
| 5,207,837 | 5/1993 | Honeycutt | 134/42 |
| 5,216,050 | 6/1993 | Sinclair | 524/108 |
| 5,227,415 | 7/1993 | Masuda et al. | 524/17 |
| 5,268,222 | 12/1993 | Honeycutt | 428/224 |
| 5,270,111 | 12/1993 | D'Haese et al. | 428/356 |
| 5,286,837 | 2/1994 | Barrows et al. | 528/291 |
| 5,300,358 | 4/1994 | Evers | 428/286 |
| 5,316,688 | 5/1994 | Gladfelter et al. | 252/90 |
| 5,359,026 | 10/1994 | Gruber | 528/354 |
| 5,389,425 | 2/1995 | Platt et al. | 428/195 |

FOREIGN PATENT DOCUMENTS

| | | | |
|---|---|---|---|
| 2093051 | 6/1994 | Canada | B32B 5/08 |
| 0530987A1 | 3/1993 | European Pat. Off. | |
| WO91/08726 | 6/1991 | WIPO | A61F 13/15 |
| WO92/01556 | 2/1992 | WIPO | B32B 31/30 |
| WO92/04410 | 3/1992 | WIPO | C08L 31/04 |
| WO92/04412 | 3/1992 | WIPO | C08L 67/04 |
| WO92/15454 | 9/1992 | WIPO | B32B 27/08 |
| WO93/11941 | 6/1993 | WIPO | B32B 27/32 |
| WO93/22125 | 11/1993 | WIPO | B29C 47/06 |
| WO93/24152 | 12/1993 | WIPO | A61L 2/26 |
| WO94/06866 | 3/1994 | WIPO | C08L 67/04 |
| WO94/07941 | 4/1994 | WIPO | C08J 5/18 |
| WO94/08078 | 4/1994 | WIPO | D01F 6/62 |

*Primary Examiner*—Christopher R. Raimund
*Attorney, Agent, or Firm*—Gary L. Griswold; Walter N. Kirn; John H. Hornickel

[57] ABSTRACT

Aqueous-alkali disposable articles are disclosed. The articles are made from films or non-woven webs or composites of films and webs where the film or nonwoven web comprises a hydrolytically degradable polymer and preferably also comprises a water soluble polymer. Multilayer microfibers of at least one layer of a hydrolytically degradable polymer and at least one layer of a water soluble polymer are particularly disclosed. The articles have water resistance during preparation, storage, and use with mammals but are dispersible when submersed in water at conditions of elevated temperature, elevated pH, and during a single commercial laundry cycle. The articles solve both the problem of solid waste disposal prevalent with single use garments and the problem of repeated cleansing and recycling of multiple use garments. Contamination associated with the articles of the invention after their use will be disinfected during the commercial laundry cycle that is utilized to disperse the article.

2 Claims, No Drawings

DISPERSIBLE COMPOSITIONS AND ARTICLES AND METHOD OF DISPOSAL FOR SUCH COMPOSITIONS AND ARTICLES

FIELD OF INVENTION

This is a division of application No. 08/367,026 filed Dec. 30, 1994, now U.S. Pat. No. 5,472,518.

This invention relates to films, composites, and other compositions that can be made into articles that are disposable through dispersal into waste water under aqueous-alkali conditions and the use of such articles, made from such compositions, as sheet-like materials that have stability during use and disperse into water as a means of disposal.

BACKGROUND OF THE INVENTION

Even though the amount of plastics used in a variety of consumer goods, packaging and medical articles has not increased over the past twenty years, the visual perception is that more and more nondegradable plastics are filling up our landfills. Plastics offer many advantages over the more traditional wood, glass, paper, and metal articles including improved performance, comparable or decreased cost of manufacture, decreased transportation costs, etc. Disposal of all waste materials including food waste, packaging materials, etc. into a typical landfill provides a relatively stable environment in which none of these is seen to decompose at an appreciable rate. Alternative waste disposal options are increasingly discussed and utilized to divert some fractions of waste from entombment. Examples of these alternatives include municipal solid waste composting, anaerobic digestion, enzymatic digestion, and waste water sewage treatment.

Developing compositions and articles which are more compatible with these waste disposal methods is a goal professed in the current art of plastics improvements.

The art has previously recognized a variety of articles designed for disposal into the toilet or water closet after use, commonly termed "flushable." Flushable articles could, but do not always, totally disperse within the waste water system. They are principally constructed to avoid clogging the waste water system. Nonwoven articles of this type are typically useful for feminine hygiene or incontinence. For example, the disposable sanitary products described in U.S. Pat. No. 3,480,016 are comprised of fibers bound together by a resin which is insoluble in water but will disperse due to water sensitivity upon disposal into the toilet. Similar structures are claimed in U.S. Pat. No. 3,804,092. Alternatively, composite flushable structures for feminine hygiene articles include those described in PCT Publication WO 91/08726 wherein an absorbent core of fibrous material is laminated to a water permeable topsheet and a water impermeable backsheet. The topsheet may be a film or a nonwoven and both the topsheet and backsheet were described as comprising polylactide or polyglycolide. Similar composite articles and uses are described by U.S. Pat. No. 5,300,358.

There exists art describing a variety of flushable articles comprised of film structures. For example, a bedpan liner was described in U.S. Pat. No. 3,546,716 which is made from a cold water soluble base film, e.g. poly(vinyl alcohol) film, coated with a water insoluble or water repellent material. The structures also contain a tissue paper covering adhered to the water insoluble coating and the preferred disposal is into the sewage system.

Another series of articles designed to be flushed into sewage treatment is described by U.S. Pat. No. 4,372,311 wherein disposable articles comprised of water soluble films coated with an insoluble material are claimed. Articles may be useful as feminine hygiene products, diaper components, or bandages. The existence of a laminate structure was noted, this being that when the coating was of sufficient thickness to have film-like properties unto itself.

The use of a water soluble film coated with or laminated to a water insoluble film as a disposable bag is described in U.S. Pat. No. 4,620,999. The claims describe a package for body waste which is stable to human waste during use but which can be made to degrade in the toilet at a rate suitable for entry into a sewage system without blockage by adding a caustic substance to achieve a pH of at least about 12. Such structures are typically a poly(vinyl alcohol) film layer coated with poly(hydroxybutryate).

A related structure is described by PCT Publication WO 92/01556. A multilayer film containing layers of water insoluble and water soluble films is described, where both layers may be made from poly(vinyl alcohol) and a difference in the extent of hydrolysis provides the differential solubility. The mechanical strength of the composite comes from the water soluble component and the resistance from water during use is derived from the water insoluble coating. Uses envisioned included diapers, cups, golf tees, and laundry bags. A later publication WO 93/22125 describes the process for making these structures and lists additional article claims for sanitary articles and articles where the insoluble coating is specifically an ink.

Compositions comprised of multilayer films are known in the art. The utility of such structures lies in the manipulation of physical properties in order to increase the stability or lifetime during use of such a structure. For example, U.S. Pat. Nos. 4,826,493 and 4,880,592 describe the use of a thin layer of hydroxybutyrate polymer as a component of a multilayer structure as a barrier film for diaper components and ostomy bags.

Others have designed multilayer films specifically to be compostable. PCT Publication WO 92/15454 describes films which are comprised of external layers of an environmentally degradable film and an internal layer of a biodegradable, water soluble film. Typically, the external layers are comprised of a polyolefin, poly(caprolactone), or ethylene vinyl acetate and the internal layer is described as poly(vinyl alcohol). One of the external layers may be a nonwoven structure. Additional art in this area is described by EPO Publication 0 616 570.

The development of a multilayer microfiber has been noted in the art. Basic technology building patents describing the process by which multilayer microfibers can be prepared are described in U.S. Pat. No. 5,207,970.

Disposal of medical waste is increasingly coming under the scrutiny of government agencies and the public alike. Concerns over the fate of materials contaminated with infectious substances are valid and proper measures to insure the safety of health care workers and the general public should be taken.

Currently, medical waste can be categorized into reusable and disposable. Reusable medical articles are cleansed and sterilized under stringent conditions to ensure disinfection. For example, reusable medical devices such as garments or drapes can be used up to 100 times. In comparison, after use, disposable medical articles are typically disinfected or sterilized, adding a significant cost, prior to disposal into a specially designated landfill or waste incinerator. Often, the disposal cost for the contaminated single use articles is quite high.

The utility of a water dispersible tape for use on reusable surgical drapes and gowns was recognized in U.S. Pat. Nos. 5,125,995 and 5,270,111. The use of a water dispersible indicator tape was recognized in PCT Publication WO 93/24152.

Furthermore, a series of U.S. Patents describes composite fabrics, utensils, packaging materials and a method for disposing garments and fabrics which are soluble in hot water, namely: U.S. Pat. Nos. 5,268,222; 5,207,827; 5,181,967; and 5,181,966. The structures described are typically comprised principally of poly(vinyl alcohol) which is only soluble above 37° C. The target disposal method for said articles is via laundering where the temperature is usually greater than 50° C.

Similar fabrics are described in Canadian Patent Publication 2,093,051. A composite structure of nonwoven layers is prepared from a poly(vinyl alcohol) component and another material which acts as a barrier layer during use. The nonwoven fabrics claimed are designed to disperse in an aqueous environment having a pH greater than 12 and a temperature greater than 70° C. in a period of less than about 10 minutes.

Generally, poly(lactic acid), its blends and several articles made thereof are described in U.S. Pat. Nos. 5,200,247; 5,227,415; 5,076,983; 5,216,050; 5,359,026; and PCT Publications WO 94/06866; WO 94/07941; WO 94/08078; WO 92/04412; and WO 92/04410 and references cited therein. No references to the utility of poly(lactic acid) in a laundry dispersible article were described.

Poly(ester amide)s are described in a series of patents by Barrows, et.al. in U.S. Pat. Nos. 5,286,837; 4,529,792; and 4,343,931. The utility of such materials in a laundry dispersible article was not realized.

SUMMARY OF THE INVENTION

The art has recognized the use of water soluble or alkali-dispersible materials or combinations thereof for articles, which can be disposed via flushing into waste water. However, the art has not recognized that novel compositions and materials and existing compositions and materials can be employed to provide a single use article that is effectively dispersed via hydrolytical degradation during a single commercial laundry cycle.

The present invention relates to the development of compositions and articles for disposal into the waste water treatment process, specifically via dispersal into an aqueous-alkali environment accompanied by elevated temperature or elevated pH or both and can include mechanical agitation.

The present invention solves the problem of disposal of articles by designing materials for a single use and then for disposal into the laundering cycle. Thus the transportation and handling costs and risks associated with disposable medical articles and the risk of incomplete disinfection of a reusable article can be eliminated.

The present invention has found that novel and existing compositions and materials can be employed as this type of article which resolves the issues confronting both single use article disposal and multiple use article recycling.

Compositions used in the present invention can be constructed from a variety of polymers and can be constructed in a variety of forms. Some of the compositions are themselves novel and some of the forms of construction are novel. All of the embodiments of the invention are novel in their use as alkali-aqueous disposable articles.

Compositions used in the invention comprise hydrolytically degradable polymers. Consistent with the definitions employed by the American Society for Testing of Materials D883 Standard Terminology Relating to Plastics, "hydrolyrically degradable" means a degradable plastic in which the degradation results from hydrolysis. A "degradable plastic" means a plastic designed to undergo a significant change in its chemical structure under specific environmental conditions resulting in a loss of some properties that may vary as measured by standard test methods appropriate to the plastic and the application in a period of time that determines its classification. It is significant to the invention that hydrolyrically degradable polymers not only disperse in aqueous-alkali conditions of a laundry but also can degrade in waste water over time regardless of pH.

Nonlimiting types of hydrolytically degradable polymers include poly(lactic acid) (hereafter "PLA"); poly(ester amide)s (hereafter "PEA"); poly(glycolic acid) (hereafter "PGA"); and poly(hydroxy butyrate-co-valorate) (hereafter "PHBV"); and the like; and combinations thereof as copolymers, blends, mixtures, and the like.

Some compositions of the invention also comprise hydrolytically degradable polymers in combination with water soluble polymers. "Water soluble" means that the polymer will completely dissolve upon extended contact with water. Nonlimiting types of water soluble polymers include poly(vinyl alcohol) (hereafter 37 PVOH"), poly(aspartic acid), poly(acrylic acid), poly(methacrylic acid), poly(acrylamide), poly(vinyl pyrrolidone), poly(alkylene oxide)s, complex carbohydrates, and combinations thereof as copolymers, blends, mixtures, and the like.

Constructions of compositions used in the present invention can include single layer films, multiple layer films, non-woven webs formed from staple fibers, non-woven webs formed from single layer microfibers, non-woven webs formed from multiple layer microfibers, and non-woven webs formed from microfibers of blended compositions.

The type of composition and the type of construction used in the present invention can be chosen according to the type of features desired for the aqueous-alkali dispersible article.

Articles of the present invention can have the following features. The article can be dispersible, and hence disposable in wastewater, when exposed to water having an elevated temperature. "Elevated temperature" means greater than or equal to 50° C.

The article can be dispersible, and hence disposable in wastewater, when exposed to water having an elevated pH. "Elevated pH" means that the pH is greater than 7. Preferably, the pH is greater than 9.5 and need not exceed 11.9 because each of the articles of the present invention will disperse at elevated temperature and during a single commercial laundry cycle into waste water at a basic pH less than 12. Commercial laundries generally avoid laundering at pH of 12 or greater because reusable fabrics can be damaged, especially polyesters.

The article can be dispersible, and hence disposable in wastewater, when exposed to water for a minimal time, such as used in a single commerial laundry cycle. "Single commercial laundry cycle" means a cycle of soaking, agitation, spinning, rinsing, and spinning that comprises about 40 minutes with the soaking and agitation durations comprising about 30 minutes.

The article can be sturdy and resistant to water during preparation, storage, and use. "Water resistant" means that the article will not significantly degrade upon contact with water, saline solution, or human body exudate such as perspiration, blood, urine, or other bodily fluids yet will be dispersible and hence disposable when exposed to water in a single commercial laundry cycle.

"Aqueous-alkali dispersible article" means that at elevated temperature, elevated pH, and that during a single commercial laundry cycle, the article substantially degrades into small pieces and substantially disperses into water. Preferably, the substantial degradation is at least 90 weight percent of the article. The small pieces should be capable of passage through the mesh screens and other filtering devices typically associated with commercial laundry facilities. Typically, the mesh screens and filtering devices can permit passage of pieces of a size not larger than about 25 mm and preferably not larger than about 12 mm and most preferably not larger than 7 min. The smaller the size of the pieces, the easier it is for the pieces to continue to hydrolytically degrade in the waste water regardless of pH.

A feature of the invention is that the articles of the invention are dispersible in an aqueous-alkali environment and yet are resistant to water during use. The articles can be formed from at least one hydrolytically degradable polymer or from a combination of polymers where one polymer is hydrolytically degradable and one polymer is water soluble. The articles function well during use because the hydrolytically degradable polymer is either water insoluble or water impermeable and prevents the water soluble polymer from dissolving upon contact with liquids or bodily fluids. Upon disposal, the water soluble polymer will enhance the rate of dissolution or destruction of the article in the aqueous-alkali environment, especially when exposed to some combination of elevated temperature, elevated pH conditions of a single commercial laundry cycle. The hydrolytically degradable polymer portion of the article will hydrolyze or otherwise degrade, allowing the water soluble polymer to dissolve and result in the entire article breaking up and dispersing into wastewater.

Another feature of the invention is that an article of the invention entirely disperses into water within a short time, at least no longer than a single commercial laundry cycle, to easily dispose of the article that has been used. The laundry cycle is known to disinfect contaminated materials; therefore there is no hazard associated with discharge of the waste water containing the dispersed article. Indeed, the wastewater can further hydrolytically degradable the hydrolytically degradable polymer, if necessary, regardless of pH. This disposal method is more convenient than if the contaminated article were to remain a solid waste requiting disinfection prior to disposal into a landfill or waste incinerator.

Another feature of the invention is that either existing compositions or constructions can be used in a new article to provide the aqueous-alkali dispersible article as used according to the present invention. Unexpectedly, some hydrolytically degradable materials will undergo sufficient degradation within one laundry cycle that the articles made therefrom can be considered dispersed.

Another feature of the invention is that novel compositions and constructions can also be used in the new aqueous-alkali dispersible articles.

Another feature of the invention is that hydrolytically degradable polymers can be used alone or with water soluble polymers in the constructions used in the invention.

Another feature of the invention is that the constructions used in the invention can be combined with reusable medical devices where only the dispersable portion of the combination is disposed while the reusable portion of the combination is recycled. The recycling and the disposal can occur in the same laundry cycle.

An advantage of the invention is that compositions and constructions of the present invention are easily manufactured.

Another advantage of the invention is that the compositions and constructions of the present invention are flexible, conformable to the mammalian body, and not irritating or allergenic to mammalian skin.

Another advantage of the invention is the ability to use the present invention to alter the manner by which articles contaminated by infectious waste are disposed from solid waste landfilling or incineration to wastewater treatment.

Briefly, one aspect of the invention is an article comprising an aqueous-alkali dispersible microfiber comprising at least one hydrolytically degradable polymer.

Another aspect of the invention is the use of a water resistant, aqueous-alkali dispersible article dispersible at elevated temperature, elevated pH, and during a single commercial laundry cycle, wherein the article comprises at least one hydrolytically degradable polymer.

Another aspect of the invention is a multilayered microfiber, comprising at least one layer of a water soluble polymer and at least one layer of at least one hydrolytically degradable polymer.

Another aspect of the invention is a method of disposing of a water resistant, aqueous-alkali dispersible article comprising at least one hydrolytically degradable polymer, comprising the step of subjecting the article to elevated temperature, elevated pH, and a single commercial laundry cycle, whereby the article disperses into wastewater.

The embodiments of the invention are further described below.

EMBODIMENTS OF THE INVENTION

Constructions of Articles of the Invention

Constructions of compositions used in the present invention can include single layer films of single polymers, single layer films of blended polymers, multiple layer films, non-woven webs formed from staple fibers, non-woven webs formed from single layer microfibers, non-woven webs formed from multiple layer microfibers, and non-woven webs formed from microfibers of blended compositions.

The constructions can be formed into aqueous-alkali dispersible articles that can be used as garments, drapes, dressings, surgical sponges, masks, diapers, sanitary articles, packaging, tapes, and disposable medical fabrics.

Films used in the invention can be formed according to techniques known to those skilled in the art. Among film forming techniques are casting, blowing, and coextrusion.

Non-woven webs useful for the invention can be formed according to techniques known to those skilled in the art. Suitable hydrolytically degradable polymers can be spun into fibers which can then be processed into non-woven sheets through a combination of web forming techniques (air laid or dry laid or wet laid) and web bonding techniques (thermal, chemical or mechanical means). Also useful are direct web forming techniques such as meltblown, spunbond, and multilayer microfiber meltblown web forming.

Once the films or non-woven webs are formed into sheets or sheet-like material, the garments, drapes, or other forms of the constructions can be sewn, adhered, or otherwise assembled according to techniques known to those skilled in the art. Among techniques used for assembling garments, drapes, and the like forms of construction include stitching, heat sealing, sonic welding, and adhesive lamination.

Compositions Used in Constructions for Articles of the Invention

Compositions used in the invention comprise hydrolytically degradable polymers. These hydrolytically degradable polymers can be employed alone and formed into films of thicknesses of 10–300 gm and preferably of a thickness of 10–125 µm. Nonlimiting examples of such hydrolytically degradable polymeric films include PLA films disclosed in U.S. Pat. Nos. 5,200,247; 5,227,415; 5,076,983; 5,216,050; and PCT Publication Nos. WO 94/06866; WO 94/07941; WO 94/08078; WO 92/04412; and WO 92/04410; (the disclosures of which are incorporated by reference herein) and PEA films disclosed in U.S. Pat. Nos. 5,286,837; 4,529,792; and 4,343,93 1; (the disclosures of which are incorporated by reference herein).

Films of hydrolytically degradable polymers can be combined with films of water soluble polymers, such as PVOH, to form two-layered films that combine the benefits of the hydrolytically degradable polymeric film to provide water resistance and of the water soluble polymeric film to enhance dispersibility of the multilayer film when subjected to a single commercial laundry cycle. The thickness of the hydrolytically degradable polymeric layer in a two-layered film can range from about 0.1 to about 250 µm and preferably from about 5 to about 150 µm. The thickness of the water soluble polymeric layer in a two-layered film can range from about 0.1 to about 250 µm and preferably from about 5 to about 150 µm. Thus, thickness of the two-layered film can range from about 5 to about 300 µm and preferably from about 10 to 125 µm.

According to the teaching of U.S. Pat. No. 4,908,278 (which is incorporated by reference herein) the overall thickness of the multilayer film can remain relatively constant while the number of layers varies. A film containing multiple layers can be constructed in this manner.

Optionally, a three layered film of a water soluble polymeric film layer sandwiched between two films of the same or different hydrolytically degradable polymeric film layers provides a composition that provides water resistance during use and then dispersal upon disposal in water.

Films of hydrolytically degradable polymers and water soluble polymers can be blended together to form a single polymeric layer. The ratio of the polymers can range from about 1:19 to about 19:1. The blended layer can have a thickness ranging from about 10 to about 300 µm.

Non-woven webs of hydrolytically degradable polymers can also be used in the present invention. Non-woven webs can comprise several constructions, some themselves being novel. Non-woven webs can be constructed from microfibers that are multi-layered or blended from two or more different polymeric compositions.

Non-woven webs of a hydrolytically degradable polymeric microfiber can be used in the present invention. A nonlimiting example of such microfiber includes a PLA blown microfiber non-woven web formed according to techniques known to those skilled in the art. Nonlimiting examples of such techniques are disclosed in PCT Publication WO 94/08078.

Non-woven webs of blended microfibers can be formed from hydrolytically degradable polymer(s) and water soluble polymer(s) according to techniques known to those skilled in the art. Nonlimiting examples of such blended microfiber nonwoven webs include blends of PVOH and PLA. Such non-woven webs can have a density of 10–200 g/m$^2$ and preferably 25–130 g/m$^2$.

Non-woven webs of multi-layered microfibers can be constructed according to techniques of the present invention. These novel compositions and constructions are especially useful in the present invention. The multi-layered microfibers can have from 2 to about 27 layers alternating of different polymers, preferably different types of polymers. Preferably, the multi-layered microfibers can have about 3–9 layers with a preference for the outermost layers of the microfiber comprising hydrolytically degradable polymers.

The different polymers can be both hydrolytically degradable polymers, such alternating layers of PLA and PHBV or alternating layers of PLA and PEA or alternating layers of PHBV and PEA. Alternatively and preferably, the different polymers are different types of polymers, with alternating layers of at least one kind of hydrolytically degradable polymer and of at least one kind of water soluble polymer. Preferably, the alternating layers comprise two polymers: one hydrolyrically degradable polymer and one water soluble polymer.

Nonlimiting examples of multilayered microfibers include PVOH as the water soluble polymer in combination with PLA, PEA, or PHBV as the hydrolyrically degradable polymer. The number of layers of the multilayered microfiber preferably ranges from 3 to 9 layers with the outermost layers being hydrolyrically degradable polymer.

The thickness of the multilayered microfiber ranges from about 1 to about 20 µm.

The extrusion feed ratio of composition in the multilayered microfiber ranges from about 9/1 to about 1/9 of hydrolyrically degradable polymer/water soluble polymer, and preferably a range from about 3/1 to about 1/3 of hydrolyrically degradable polymer/water soluble polymer.

A particularly preferred multilayered microfiber composition of the present invention is a three-layered microfiber having a composition of 75/25 PLA/PVOH, where PLA forms the two outside layers. At this extrusion feed ratio, a PLMPVOH/PLA microfiber non-woven web has particularly preferred mechanical strength for the formation of an aqueous-alkali dispersible article.

Other multilayered microfiber compositions of the present invention comprise PHBV/PVOH/PHBV multilayered microfibers, PHBV/PLA multilayered microfibers, and PEA/PVOH/PEA multilayered microfibers.

Multilayered microfiber non-woven webs of the invention are prepared according to the preferred process described in U.S. Pat. No. 5,207,970 (Joseph et al.) which is incorporated herein by reference. The process utilizes the apparatus shown in FIG. 1 of U.S. Pat. No. 5,207,970 wherein the polymefic components are introduced into the die cavity of the die from a separate splitter, splitter region or combining manifold and into e.g., the splitter from extruders. Gear pumps and/or purgeblocks can also be used to finely control the polymer flow rate. In the splitter or combining manifold, the separate polymeric component flowstreams are formed into a single layered flowstream. However, preferably, the separate flowstreams are kept out of direct contact for as long a period as possible prior to reaching the die.

The split or separate flowstreams are combined only immediately prior to reaching the die, or die orifices. This minimizes the possibility of flow instabilities forming in the separate flowstreams after being combined from the single layered flow streams, which would tend to result in nonuniform and discontinuous longitudinal layering in the multi-layered microfibers.

From the die cavity, the multi-layer polymer flowstream is extruded through an array of side-by-side orifices. Prior to this extrusion, the feed can be formed into the appropriate profile in the cavity, suitably by use of a conventional coathanger transition piece. Air slots are disposed on either side of the row of orifices for directing uniformly heated air at high velocity at the extruded layered melt streams. The air temperature is generally about that of the meltstream, although preferably 20° C. to 30° C. higher than the polymer melt temperature. This hot, high-velocity air draws out and attenuates the extruded polymeric material, which will generally solidify after traveling a relatively short distance from the die. The solidified or partially solidified fibers are then formed into a web by known methods and collected.

Most of the hydrolytically degradable polymers are commercially available. PHBV (−18) is commercially available from Zeneca Biopolymers of Wilmington, Del. PLA is available as ECOPLA™ Resin Lots 18, 19, 20, 23, and 51 from Cargill, Incorporated of Minneapolis, Minn. and otherwise disclosed in U.S. Pat. No. 5,359,026. PEA is prepared according to U.S. Pat. Nos. 5,286,837; 4,529,792; and 4,343,931.

Water soluble polymers are commercially available. PVOH is commercially available from Air Products of Allentown, Pa. as Vinex 2019, Vinex 2034, or Vinex 2144 resins or as Airvol 125 or 325 resins.

Optional other materials can be added to the compositions and constructions used in the present invention to impart additional properties to the resulting articles. Nonlimiting examples of other materials include plasticizers, antimicrobial agents, and fluid repellents.

Nonlimiting examples of plasticizers include triethyl citrate, alkyl lactates, triacetin, alkyl glycols, and oligomers of the base polymer and can be present in a mounts ranging from about 1 to about 50 weight percent of the final composition and preferably in an amount ranging from about 5 to about 30 weight percent.

Antimicrobial agents are known to those skilled in the art. While it is not presently known which specific antimicrobial agents, antifungal agents, and the like would be compatible in these constructions and compositions of the present invention, nonlimiting examples might include chlorhexidine glucanate, iodophores, pyrithiones, isothiazolines, or benzimidazoles. These agents may be present in amounts ranging from about 0.2 parts per million to about 3000 parts per million depending on the agent and based on the total composition.

Nonlimiting examples of fluid repellents include fluoroehemicals such as oxazolidinones disclosed in U.S. Pat. Nos. 5,025,052 and 5,099,026, silicones and waxes and are present in amounts ranging from about 0.5 to about 5 weight percent of the final composition and preferably in an amount ranging from about 0.5 to about 2 weight percent.

Composites of the films and non-woven webs described above can be combined and used as articles according to the present invention. Nonlimiting examples of possible composite constructions include a non-woven web of a hydrolytically degradable polymer laminated to a film of a water soluble polymer. Particularly, a blown microfiber web of either PLA or PEA can be laminated to a PVOH film to provide a composite that has similar properties of water resistance during use and dispersibility when subjected to aqueous-alkali conditions as the PLA/PVOH film or the PLA/PVOH multilayered microfiber non-woven web described above. Conversely, a film of a hydrolytically degradable polymer laminated to a non-woven web of a water soluble polymer could also be constructed.

One skilled in the art would understand that the possible combinations of films and webs and the compositions of such films and webs are not limited to those possibilities presented here. The present invention contemplates the use of hydrolytically degradable polymers in a variety of forms alone or in combination with water soluble polymers in a variety of forms to be used in the assembly of articles that have water resistance during preparation, storage, and use but are dispersible when submersed in water under elevated temperature, elevated pH, and during no more than a single commercial laundry cycle.

Other nonlimiting examples include composites of a hydrolytically degradable nonwoven web laminated to another hydrolytically degradable nonwoven web or film. The invention includes all of the various composites possible from the films and nonwoven webs described herein.

Usefulness of the Invention

The invention provides great utility where water resistance of an article is needed during use, but disposal via water treatment such as laundering is employed. Examples of such uses include surgical non-wovens and films such as drapes, gowns, dressings, masks, surgical sponges, packaging, tape backings, and sanitary articles, where water resistance is critical to performance of the article but where disposal of contaminated articles, requires special handling.

The present invention is superior to PVOH films and nonwovens that having a high degree of hydrolysis. Those particular grades of PVOH are required in order to maintain performance during use if there exists the potential of fluid contact during use. However, these same grades of PVOH are not readily soluble at temperatures typically found in hospital laundry facilities, thereby limiting their usefulness as a dispersible article. In contrast, the articles of the present invention are dispersible under conditions typical of hospital laundry facilities, those being aqueous-alkali solution of pH of greater than 9.5 but typically less than 12.0 and a temperature of 70° C.

Hydrolyrically degradable materials used in the present invention exhibit sufficient performance during use yet disperse in a hospital laundry. In some embodiments, the invention can also contain a water soluble material, such combination of materials expanding the range of useable water soluble materials (i.e., cold water soluble PVOH) materials by maintaining adequate performance during use.

The articles of the present invention will disperse in typical laundry conditions. After the hydrolytically degradable polymer is initally degraded in the aqueous-alkali laundry conditions, it is further hydrolytically degradable, if necessary, by water in the waste water and preferably consumed by natively occurring microorganisms in the waste water. In the preferred embodiments, the water soluble polymer is also biodegradable. The downstream disposal of laundered waste is typically a waste water treatment facility, where a broad spectrum of organism cultures are known to exist.

Another use of the invention is the combination of an aqueous-alkali dispersible article and a reusable medical device, such as a garment or drape, where the aqueous-alkali dispersible article is dispersible and the reusable medical device is recyclable. Nonlimiting arrangements of the two articles could include overlaying, overlapping, and contiguous constructions where the section of the combination to be discarded is the dispersible article. After one use, another dispersible article can be sewn, adhered with an aqueous-alkali dispersible adhesive, or sonic welded to the reuseable article.

Further aspects of the invention are disclosed in the examples below.

Test Methods

BASIS WEIGHT FOR BLOWN MICROFIBER WEBS

A 10×10 centimeter (cm) sample was cut from the microfiber web and weighed to the nearest ±0.001 g. The weight was multiplied by 100 and reported as basis weight in g/m$^2$.

LAUNDERING WEIGHT LOSS TEST

A 5–50 gram sample of film or nonwoven substrate was weighed, and placed into a 61×91.5 cm mesh laundry bag with the mesh pores being about 7 mm in diameter. The bag was then folded down twice, and in on itself twice, then sealed with a 114 mm mesh bag laundry pin. The pin and the mesh bag are commercially available from Minnesota Chemical Company, St. Paul, Minn. The mesh bag is place into a 60 lbs-type (27 kg) commercial washing machine (Milnor washer, Model No. 36021bwe/aea; Pillerin Milnor Corp., Kennet, La.). The samples were then washed using a typical laundry cycle for surgical linens. The cycle includes (a) a three minute alkali cold water break, using 0.1% Paralate 55 GL11™ m Commercial Liquid Laundry Alkali (Ecolab Inc. St. Paul, Minn.) (b) a three minute cold water rinse (c) an eight minute hot water detergent & alkali step, at 54.4° C. using 0.1% Paralate 55GL11™ Commercial Liquid Laundry Alkali, and 0.05% Kindet™ Commercial Liquid Laundry Detergent (Ecolab Inc.) St. Paul, Minn.)., (d) two three minute hot water rinses at 71° C., (e) a three minute warm water rinse at 43.3° C., (f) a three minute cold water rinse, (g) a four minute cold water sour/soft using 0.05% Tri Liquid Sour 55GL™ (Ecolab Inc.), and 0.05% Tex Special Liquid™ Commercial Liquid Denim Lubricant/Softener (Ecolab Inc.), and (h) a high speed extraction.

Each bag is then opened, and the weight of any remaining material is measured. Any material losing more than 90% of its original mass is considered acceptable.

BEAKER TEST

In a 20° C., 75% R.H. room a 20 cm×20 cm section of substrate is placed over the top of a 500 cm$^3$ beaker. The sample is placed in the beaker with approximately a 25 mm depth of concave material sag into the beaker. The outer edges of the material are secured to the beaker using a rubber band. 10 cm$^3$ of tap water is poured into the concave section of the substrate. The time for the integrity of the film to be compromised is observed and is reported.

TENSILE STRENGTH

Tensile modulus data on the multi-layer microfiber webs was obtained according to ASTM D882-91 "Standard Test Method for Tensile Properties of Thin Plastic Sheeting" using an Instron Tensile Tester (Model 1122), Instron Corporation, Canton, Mass. with a 50.8 mm jaw gap and a crosshead speed of 25.4 cm/min. Web samples were 2.54 cm in width.

Examples

Non-woven webs of microfibers were prepared according to the following technique:

The multi-layered blown microfiber webs of the present invention were prepared using a melt-blowing process as described in U.S. Pat. No. 5,207,970 (Joseph et al.) which is incorporated herein by reference. The process used a melt-blowing die having circular smooth surfaced orifices (10 per cm) with a 5/1 length/diameter ratio.

Examples 1–29 and Comparison Examples C1≧C8 were prepared with different formulations shown in Table 1 below. These examples were prepared using two extruders having different temperatures, a die block having a different temperature, using conditions having an air temperature, an air gap, and a collector distance. Each of the extruder, die block, and air temperatures in ° C. and the air gap and collector distances in cm for each example and comparison example are identified in Table 2 below.

The first extruder with each zone having a temperature shown in Table 2 delivered a melt stream of Resin 1 shown in Table 1 for each example to the feedblock assembly. The second extruder with zone having a temperature shown in Table 2 delivered a melt stream of Resin 2, (if a Resin 2 was used) shown in Table 1 for each example to the feedblock. The feedblock having a temperature of the higher of the two extruder temperatures split the two melt streams. The polymer melt streams were merged in an alternating fashion into a multiple layer melt stream on exiting the feedblock, with Resin 1 being the outermost layers or odd numbered layer(s) and Resin 2 (if any) being the innermost or even numbered layer(s). The gear pumps were adjusted so that the extrusion feed ratio of Resin 1/Resin 2 was delivered to the feedblock assembly as given in Table 1. A 0.14 kg/hr/cm die width polymer throughput rate was maintained at the die also having a temperature of the higher of the two extruder temperatures. The air temperature was maintained at a temperature as shown in Table 2 and at a pressure suitable to produce a uniform web with an air gap distance also shown in Table 2. Webs were collected at a collector-to-die distance also shown in Table 2 for each example and comparison example. The resulting microfiber webs, comprising multilayer microfibers as shown in Table 1, having an average diameter of less than about 10 μm, had a basis weight also as shown in Table 1.

In some Examples, FCO, (fluorochemical oxazolidinone) is an additive to Resin in weight percent of Resin 1.

TABLE 1

| EXAMPLE | FORM | LAYERS | RESIN 1 ODD LAYER | RESIN 2 EVEN LAYER | FEED RATIO | RESIN 1 ADDITIVE | BASIS WEIGHT (g/m$^2$) |
|---|---|---|---|---|---|---|---|
| 1 | BMF | 1 | PLA-L18 | — | | | 115 |
| 2 | BMF | 1 | PLA-L18 | — | | 1% FCO | 102 |

TABLE 1-continued

| EXAMPLE | FORM | LAYERS | RESIN 1 ODD LAYER | RESIN 2 EVEN LAYER | FEED RATIO | RESIN 1 ADDITIVE | BASIS WEIGHT (g/m$^2$) |
|---|---|---|---|---|---|---|---|
| 3 | BMF | 1 | PLA-L18 | — | | 2% FCO | 78 |
| 4 | BMF | 3 | PLA-L18 | PVOH-2019 | 75:25 | | 111 |
| 5 | BMF | 3 | PLA-L18 | PVOH-2019 | 50:50 | | 112 |
| 6 | BMF | 3 | PLA-L18 | PVOH-2019 | 25:75 | | 95 |
| 7 | BMF | 2 | PLA-L18 | PVOH-2019 | 50:50 | | 108 |
| 8 | BMF | 2 | PLA-L18 | PVOH-2019 | 50:50 | 2% FCO | 111 |
| 9 | BMF | 5 | PLA-L18 | PVOH-2019 | 50:50 | | 105 |
| 10 | BMF | 5 | PLA-L18 | PVOH-2019 | 90:10 | | 107 |
| 11 | BMF | 5 | PLA-L18 | PVOH-2019 | 75:25 | | 109 |
| 12 | BMF | 5 | PLA-L18 | PVOH-2019 | 25:75 | | 104 |
| 13 | BMF | 5 | PLA-L18 | PVOH-2019 | 10:90 | | 107 |
| 14 | BMF | 5 | PLA-L18 | PVOH-2019 | 75:25 | 2% FCO | 108 |
| 15 | BMF | 5 | PLA-L18 | PVOH-2019 | 50:50 | 2% FCO | 104 |
| 16 | BMF | 5 | PLA-L18 | PVOH-2019 | 25:75 | 2% FCO | 112 |
| 17 | BMF | 5 | PHBV-18 | PVOH-2019 | 50:50 | | 135 |
| 18 | BMF | 5 | PHBV-18 | PVOH-2019 | 75:25 | | 134 |
| 19 | BMF | 5 | PHBV-18 | PVOH-2019 | 25:75 | | 181 |
| 20 | BMF | 1 | PLA-L18 | — | | | 102 |
| 21 | BMF | 1 | PLA-L23 | — | | | 100 |
| 22 | BMF | 1 | PLA-L51 | — | | | 106 |
| 23 | BMF | 1 | PLA-L20 | — | | | 106 |
| 24 | BMF | 3 | PLA-L18 | PVOH-2019 | 50:50 | | 90 |
| 25 | BMF | 3 | PLA-L23 | PVOH-2019 | 50:50 | | 95 |
| 26 | BMF | 3 | PLA-L51 | PVOH-2019 | 50:50 | | 97 |
| 27 | BMF | 3 | PLA-L20 | PVOH-2019 | 50:50 | | 99 |
| 28 | BMF | 1 | PEA-2,6 | — | | | 70 |
| 29 | BMF | 3 | PVOH-2019 | PHBV-18 | 50:50 | | 100 |
| C1 | BMF | 1 | PVOH-2019 | — | | | 116 |
| C2 | BMF | 1 | PVOH-2019 | — | | 1% FCO | 116 |
| C3 | BMF | 5 | PLA-L18 | PCL | 75:25 | | 128 |
| C4 | BMF | 5 | PLA-L18 | PCL | 25:75 | | 149 |
| C5 | BMF | 5 | PCL | PVOH-2019 | 25:75 | | 55 |
| C6 | BMF | 5 | PCL | PVOH-2019 | 50:50 | | 101 |
| C7 | BMF | 3 | PCL | PVOH-2019 | 50:50 | | 97 |
| C8 | BMF | 3 | PVOH-2019 | PCL | 50:50 | | 102 |

BMF means blown microfiber web.
PLA-L(n) means the lot of poly(lactic acid) of ECOPLA™ Lot Resin from Cargill, Incorporated.
PVOH-2019 means Vinex 2019 poly(vinyl alcohol) from Air Products.
PHBV-18 means poly(hydroxy butyrate-co-valorate) from Zeneca Biopolymers.
PCL means poly(caprolactone) resin Tone™ 767P, available from Union Carbide, Danbury, Conn.
PEA-2,6 means a poly(ester amide) prepared according to Example 6 from U.S. Pat. No. 5,286,837.

TABLE 2

| EXAMPLE | RESIN 1 EXTRUDER TEMP | RESIN 2 EXTRUDER TEMP | AIR TEMP | AIR GAP | COLLECTOR DISTANCE |
|---|---|---|---|---|---|
| 1 | 230 | — | 228 | 0.071 | 19.05 |
| 2 | 230 | — | 239 | 0.071 | 19.05 |
| 3 | 230 | — | 242 | 0.071 | 19.05 |
| 4 | 230 | 210 | 235 | 0.071 | 19.05 |
| 5 | 230 | 210 | 235 | 0.071 | 19.05 |
| 6 | 230 | 210 | 235 | 0.071 | 19.05 |
| 7 | 230 | 210 | 234 | 0.076 | 19.05 |
| 8 | 230 | 210 | 234 | 0.076 | 19.05 |
| 9 | 230 | 210 | 242 | 0.076 | 19.05 |
| 10 | 230 | 210 | 242 | 0.076 | 19.05 |
| 11 | 230 | 210 | 242 | 0.076 | 19.05 |
| 12 | 230 | 210 | 242 | 0.076 | 19.05 |
| 13 | 230 | 210 | 242 | 0.076 | 19.05 |
| 14 | 230 | 210 | 242 | 0.076 | 19.05 |
| 15 | 230 | 210 | 242 | 0.076 | 19.05 |
| 16 | 230 | 210 | 242 | 0.076 | 19.05 |
| 17 | 185 | 210 | 215 | 0.076 | 19.05 |
| 18 | 185 | 210 | 215 | 0.076 | 19.05 |
| 19 | 185 | 210 | 215 | 0.076 | 19.05 |
| 20 | 230 | — | 235 | 0.076 | 19.05 |
| 21 | 230 | — | 242 | 0.076 | 19.05 |

TABLE 2-continued

| EXAMPLE | RESIN 1 EXTRUDER TEMP | RESIN 2 EXTRUDER TEMP | AIR TEMP | AIR GAP | COLLECTOR DISTANCE |
|---|---|---|---|---|---|
| 22 | 230 | — | 242 | 0.076 | 19.05 |
| 23 | 230 | — | 242 | 0.076 | 19.05 |
| 24 | 230 | 210 | 236 | 0.076 | 19.05 |
| 25 | 230 | 210 | 236 | 0.076 | 19.05 |
| 26 | 230 | 210 | 236 | 0.076 | 19.05 |
| 27 | 230 | 210 | 236 | 0.076 | 19.05 |
| 28 | 180 | — | 191 | 0.076 | 22.86 |
| 29 | 215 | 185 | 213 | 0.076 | 12.7 |
| C1 | 210 | — | 246 | 0.076 | 19.05 |
| C2 | 210 | — | 235 | 0.076 | 19.05 |
| C3 | 220 | — | 239 | 0.076 | 19.05 |
| C4 | 220 | — | 239 | 0.076 | 19.05 |
| C5 | 190 | 210 | 210 | 0.076 | 26.67 |
| C6 | 190 | 210 | 212 | 0.076 | 26.67 |
| C7 | 190 | 210 | 210 | 0.076 | 26.67 |
| C8 | 210 | — | 215 | 0.076 | 12.7 |

Films were prepared according to the following technique:

The multilayer films of Examples 30–37 and Comparison Example C9 were produced using two single screw extruders feeding into a dual manifold die according to the technique described in U.S. Pat. No. 4,908,278, the disclosure of which is incorporated by reference. Both extruders were 3.175 cm (1.25 inch) diameter Killion extruders with 24:1 L/D ratios (Killion Company, Verona, N.J.). Each extruder had four equal length, independently heatable zones. The die was a 35.6 cm (14 inch) wide, 15.2 cm (6 inch) deep dual manifold die with a 5.1 cm (2 inch) wide land area. The screw rpm rates were adjusted to give the desired layer thickness. The extruder zone temperatures and die block temperature for each of the examples are shown in Table 4 below.

PVOH-2144 means Vinex 2144 poly(vinyl alcohol) from Air Products.

PVOH-2034 means Vinex 2034 poly(vinyl alcohol) from Air Products.

ENVIROPLASTIC C means a compostable polymede material available from Planet Polymer Technologies, Inc. of San Diego, Calif.

ENVIROPLASTIC H means a water dispersible polymeric material available from Planet Polymer Technologies, Inc. of San Diego, Calif.

TABLE 3

| EXAMPLE | FORM | LAYERS | RESIN 1 ODD LAYER | RESIN 2 EVEN LAYER | FILM THICKNESS |
|---|---|---|---|---|---|
| 30 | FILM | 2 | PLA-L18 | PVOH-2034 | 0.036 mm/0.05 mm |
| 31 | FILM | 2 | PLA-L18 | PVOH-2034 | 0.025 mm/0.05 mm |
| 32 | FILM | 2 | PLA-L18 | PVOH-2034 | 0.018 mm/0.05 mm |
| 33 | FILM | 2 | PLA-L18 | PVOH-2144 | 0.023 mm/0.061 mm |
| 34 | FILM | 2 | PLA-L18 | PVOH-2144 | 0.015 mm/0.061 mm |
| 35 | FILM | 2 | PLA-L19 | PVOH-2144 | 0.025 mm/0.064 mm |
| 36 | FILM | 2 | PLA-L19 | PVOH-2144 | 0.018 mm/0.064 mm |
| 37 | FILM | 2 | PLA-L19 | PLA-PVOH* | 0.020 mm/0.056 mm |
| C9 | FILM | 1 | PVOH-2034 | | 0.127 mm |
| C10 | FILM | 1 | ENVIROPLASTIC C | | 0.102 mm |
| C11 | FILM | 1 | ENVIROPLASTIC H | | 0.102 mm |

*hopper blend of 25% PLA-L19 and 75% PVOH-2144

PLA-L(n) means the lot of poly(lactic acid) of ECOPLA™ Lot Resin from Cargill, Incorporated.

TABLE 4

| EXAMPLE | RESIN 1 TEMPS | | | | RESIN 2 TEMPS | | | | DIE TEMP |
|---|---|---|---|---|---|---|---|---|---|
| | Z1 | Z2 | Z3 | Z4 | Z1 | Z2 | Z3 | Z4 | |
| 30 | 104 | 143 | 157 | 157 | 171 | 193 | 193 | 193 | 199 |
| 31 | 104 | 143 | 157 | 157 | 171 | 193 | 193 | 193 | 199 |
| 32 | 104 | 143 | 157 | 157 | 171 | 193 | 193 | 193 | 199 |

TABLE 4-continued

| EXAMPLE | RESIN 1 TEMPS | | | | RESIN 2 TEMPS | | | | DIE TEMP |
|---|---|---|---|---|---|---|---|---|---|
| | Z1 | Z2 | Z3 | Z4 | Z1 | Z2 | Z3 | Z4 | |
| 33 | 104 | 143 | 157 | 157 | 179 | 193 | 193 | 193 | 199 |
| 34 | 104 | 143 | 157 | 157 | 179 | 193 | 193 | 193 | 199 |
| 35 | 104 | 143 | 157 | 157 | 179 | 193 | 193 | 193 | 199 |
| 36 | 104 | 143 | 157 | 157 | 179 | 193 | 193 | 193 | 199 |
| 37 | 104 | 143 | 157 | 157 | 179 | 193 | 193 | 193 | 199 |
| C9 | 171 | 193 | 193 | 193 | — | — | — | — | 199 |

Comparison Example C10 and C11 were prepared as cast films from the polymer melt using a Haake extruder (commercially available from Haake GmbH of Saddlebrook, N.J.) having a 3/4" (1.9 cm) screw and a L/D ratio of 25/1. Comparison example C10 is the Enviroplastic C material described above. A 0.102 mm thick film was extruded as described above at temperatures in ° C. of zones 1–3 and die being 138, 185, 204, and 204, respectively, producing a melt temperature of 147. The chilled chrome roll was held at 10° C.

Comparison Example C11 is the Enviroplastic H material described above. A 0.102 mm thick film was extruded as described above at temperatures in ° C. of zones 1–3 and die being 138, 185, 232, and 232, respectively, producing a melt temperature of 156. The chilled chrome roll was held at 10° C. The blown microfiber webs and films of Examples 1–37 and Comparison Examples C1–C11 prepared as described above were then subjected to the Laundry Weight Loss Test and the Beaker Test. The test results are shown in Table 5 below.

TABLE 5

| EXAMPLE | LAUNDERING WT. LOSS | BEAKER TEST |
|---|---|---|
| 1 | 100.00% | >24 HRS |
| 2 | 100.00% | >24 HRS |
| 3 | 100.00% | >24 HRS |
| 4 | 97.90% | >24 HRS |
| 5 | 100.00% | >24 HRS |
| 6 | 100.00% | >24 HRS |
| 7 | 100.00% | >24 HRS |
| 8 | 100.00% | >24 HRS |
| 9 | 100.00% | >24 HRS |
| 10 | 100.00% | >24 HRS |
| 11 | 100.00% | >24 HRS |
| 12 | 100.00% | >24 HRS |
| 13 | 100.00% | >24 HRS |
| 14 | 100.00% | >24 HRS |
| 15 | 100.00% | >24 HRS |
| 16 | 100.00% | >24 HRS |
| 17 | 100.00% | >24 HRS |
| 18 | 100.00% | >24 HRS |
| 19 | 100.00% | >24 HRS |
| 20 | 100.00% | >24 HRS |
| 21 | 100.00% | >24 HRS |
| 22 | 100.00% | >24 HRS |
| 23 | 100.00% | >24 HRS |
| 24 | 100.00% | >24 HRS |
| 25 | 100.00% | >24 HRS |
| 26 | 100.00% | >24 HRS |
| 27 | 100.00% | >24 HRS |
| 28 | 100.00% | >24 HRS |
| 29 | 100.00% | >24 HRS |
| C1 | 100.00% | 5 SEC |
| C2 | 100.00% | 5 SEC |
| C3 | 35.00% | >24 HRS |
| C4 | −4.80% | >24 HRS |
| C5 | 5.10% | >24 HRS |
| C6 | 5.20% | >24 HRS |
| C7 | 5.60% | >24 HRS |
| C8 | 6.40% | >24 HRS |
| 30 | 96.90% | >24 HRS |
| 31 | 99.30% | >24 HRS |
| 32 | 97.70% | >24 HRS |
| 33 | 94.70% | >24 HRS |
| 34 | 96.40% | >24 HRS |
| 35 | 96.50% | >24 HRS |
| 36 | 92.20% | >24 HRS |
| 37 | 98.70% | >24 HRS |
| C9 | 100.00% | 2 MIN |
| C10 | −44.70% | >24 HRS |
| C11 | 2.40% | >24 HRS |

Each Examples 1–29 blown microfiber webs passed both the Laundering Weight Loss and the Beaker Test whereas Comparison Examples C1–C8 failed either one or both of the Tests. Each of Examples 30–37 films passed both the Laundering Weight Loss and the Beaker Test whereas Comparison Examples C9–C11 failed either one or both of the Tests. Both blown microfiber web and film constructions of the present invention are unexpectedly superior to known and available web and film constructions.

The blown microfiber webs and films of Examples 1–6 and Comparison Examples C1–C2 prepared as described above were then subjected to the Tensile Strength Test. The test results are shown in Table 6 below.

TABLE 6

| EXAMPLE | TENSILE STRENGTH (g/2.54 cm) |
|---|---|
| 1 | 204 |
| 2 | 508 |
| 3 | 322 |
| 4 | 1044 |
| 5 | 754 |
| 6 | 849 |
| C1 | 145 |
| C2 | 100 |

The blown microfiber webs of Examples 1–6 were unexpectedly superior to the webs of Comparison Examples C1 and C2. Comparison Examples C1 and C2 were considered to be dispersible according to the Laundering Weight Loss Test but failed the Beaker Test. Further, Comparison Examples C1 and C2 were deficient in tensile strength performance. Thus, the blown microfiber webs of Examples 1–6 show clear advantage in the construction of articles of the present invention for use in surgical and medical devices as described above. Further the tensile strengths of Examples 1–3 (PLA) were greater than the tensile strengths of Comparison Examples C1–C2 (PVOH). Yet when the two compositions were combined in a three layer microfiber of Examples 4–6 (PLA/PVOH/PLA), the tensile strengths were unexpectedly several times greater than either PLA or PVOH, or the sum of them. The constructions and compositions of Examples 4–6 are preferred for being water resistant and yet dispersible in laundries, and for their truly unexpected excellent tensile strength properties.

While not being limited to foregoing discussion of the embodiments of the invention and the examples of the embodiments, the claims of the invention follow.

What is claimed is:

1. An article comprising an aqueous-alkali dispersible microfiber, said microfiber comprising at least one hydrolyrically degradable polymer and a water soluble polymer.

2. The article of claim 1, wherein the microfiber is a blend of the hydrolytically degradable polymer and the water soluble polymer.

* * * * *